United States Patent
Saito et al.

(10) Patent No.: US 7,170,602 B2
(45) Date of Patent: Jan. 30, 2007

(54) PARTICLE MONITORING DEVICE AND PROCESSING APPARATUS INCLUDING SAME

(75) Inventors: Susumu Saito, Nirasaki (JP); Yoshihiro Hashimoto, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 75 days.

(21) Appl. No.: 11/082,652

(22) Filed: Mar. 18, 2005

(65) Prior Publication Data
US 2005/0264810 A1  Dec. 1, 2005

Related U.S. Application Data

(60) Provisional application No. 60/589,830, filed on Jul. 22, 2004.

(30) Foreign Application Priority Data
Apr. 8, 2004  (JP) .............................. 2004-114257

(51) Int. Cl.
*G01N 15/02* (2006.01)
(52) U.S. Cl. ..................................... 356/338
(58) Field of Classification Search ..................... None
See application file for complete search history.

(56) References Cited

U.S. PATENT DOCUMENTS 5,153,674 A * 10/1992 Bobel et al. ................ 356/336
5,316,983 A * 5/1994 Fujimori et al. ............. 356/335
5,861,951 A   1/1999 Uesugi et al.
6,165,312 A   12/2000 Smith, Jr. et al.

FOREIGN PATENT DOCUMENTS

| JP | 10-10036 | 1/1998 |
| JP | 11-337472 | 12/1999 |
| KR | 10-2004-0070674 | 8/2004 |

\* cited by examiner

*Primary Examiner*—Tu T. Nguyen
(74) *Attorney, Agent, or Firm*—Oblon, Spivak, McClelland, Maier & Neustadt, P.C.

(57) ABSTRACT

A particle monitoring device includes a light source for emitting a measurement light; and a light projecting/receiving unit, connected to a depressurized vessel of a processing apparatus, for projecting the emitted measurement light into the depressurized vessel and receiving a scattered light from a particle floating in the depressurized vessel. The light projecting/receiving unit is disposed such that the scattered light is received substantially parallel to the measurement light. The particle monitoring device further includes a received light intensity detection unit. The received light intensity detection unit has a received light intensity detection unit for determining whether or not the detected intensity is greater than a predetermined value and an instruction unit for instructing the processing apparatus to start, continue or stop a processing operation of the processing apparatus depending on the determined result.

8 Claims, 4 Drawing Sheets

PARTICLE MONITORING DEVICE AND PROCESSING APPARATUS INCLUDING SAME

CROSS-REFERENCE TO RELATED APPLICATIONS

This application claims priority to U.S. Provisional Application No. 60/589,830, filed on Jul. 22, 2004, and JP 2004-114257, filed on Apr. 8, 2004. These applications are incorporated herein by reference in their entirety.

FIELD OF THE INVENTION

The present invention relates to a particle monitoring device and a processing apparatus including the particle monitoring device; and, more particularly, to a particle monitoring device for monitoring particles floating in a depressurized vessel and a processing apparatus including the particle monitoring device.

BACKGROUND OF THE INVENTION

Conventionally, in manufacturing, e.g., a device or a liquid crystal, contamination of an object to be processed, which is used for the device or the liquid crystal, by particles generated in a manufacturing process thereof has been a difficult problem to be solved. In order to reduce the contamination of the object, there has been developed a particle monitoring device for monitoring a status of a particle generation.

For example, as shown in FIG. 4, the particle monitoring device includes a laser beam source 83 having a YAG laser and a secondary harmonic wave generator 80 thereof, the laser beam source introducing a laser beam 81 into a processing apparatus 82; and a two dimensional light detector 87 as a scattered light receiver for measuring via an interference filter 86 a scattered light 85 that is generated by the laser beam 81 being scattered by particles 84 floating in a processing chamber of the processing apparatus. The laser beam 81 has, e.g., a wavelength of 532 nm, and it is shaped into a sheet form in a vertical plane to be introduced into the processing apparatus 82. When it is determined by a data processor 88 that a scattered light 85 received by the two dimensional light detector 87 is of an intensity higher than a predetermined value, the scattered light receiving time of the detector 87 is prolonged from 100 ns to 200 ns.

As described above, in the particle monitoring device using a laterally scattered light, a light receiving unit such as the two dimensional light detector 87 is disposed in a direction making about 90 degrees with respect to a projection direction of the laser beam from a light projecting unit such as the laser beam source 83. Further, in a particle monitoring device using a so-called forwardly scattered light, the light receiving unit such as the two dimensional light detector 87 is disposed in a direction making about 30~60 degrees with respect to the projection direction of the laser beam.

(Reference document 1) U.S. Pat. No. 5,861,951

However, in case an exhaust section, which is provided in a processing chamber as a depressurized vessel to exhaust the inner space of the processing chamber, is extremely large, it is necessary to install the light projecting unit and the light receiving unit inside the exhaust section in order to increase the sensitivity to a scattered light generated by particles. Accordingly, the volume occupied by the light projecting unit and the light receiving unit in the exhaust section is increased, resulting in a decrease in an exhaust conductance to thereby deteriorate an exhaust capability of the processing apparatus.

SUMMARY OF THE INVENTION

It is, therefore, an object of the present invention to provide a particle monitoring device capable of monitoring particles floating in a depressurized vessel without deteriorating an exhaust capability of a processing apparatus, and a processing apparatus including the particle monitoring device.

In accordance with an aspect of the present invention, there is provided a particle monitoring device for monitoring particles in a depressurized space, the particle monitoring device being provided to a processing apparatus, having a depressurized vessel, for processing an object to be processed in the depressurized space demarcated from the depressurized vessel, the particle monitoring device including: a light source for emitting a measurement light; and a light projecting/receiving unit, connected to the depressurized vessel, for projecting the emitted measurement light into the depressurized vessel and receiving a scattered light from a particle floating in the depressurized vessel, wherein the light projecting/receiving unit is disposed such that the scattered light is received substantially parallel to the measurement light.

Preferably, the particle monitoring device further includes a received light intensity detection unit for detecting intensity of the scattered light received by the light projecting/receiving unit, wherein the received light intensity detection unit includes a received light intensity judgment unit for determining whether or not the detected intensity is greater than a predetermined value and an instruction unit for instructing the processing apparatus to start, continue or stop a processing operation of the processing apparatus depending on the determined result.

Preferably, the depressurized vessel includes an exhaust section for exhausting the depressurized space thereof, and the light projecting/receiving unit is connected to the exhaust section.

Preferably, the light projecting/receiving unit is an optical fiber.

Preferably, the measurement light is further emitted as a phase conjugate light.

Preferably, the depressurized vessel is a processing chamber for a plasma processing.

Preferably, the light projecting/receiving unit is disposed such that the scattered light is received approximately coaxial with the measurement light.

In accordance with another aspect of the present invention, there is provided a processing apparatus including the aforementioned particle monitoring device.

BRIEF DESCRIPTION OF THE DRAWINGS

The above and other objects and features of the present invention will become apparent from the following description of preferred embodiments, given in conjunction with the accompanying drawings, in which.

DETAILED DESCRIPTION OF THE
PREFERRED EMBODIMENTS

Hereinafter, a preferred embodiment of the present invention will be described with reference to the accompanying drawings.

Figure 1:
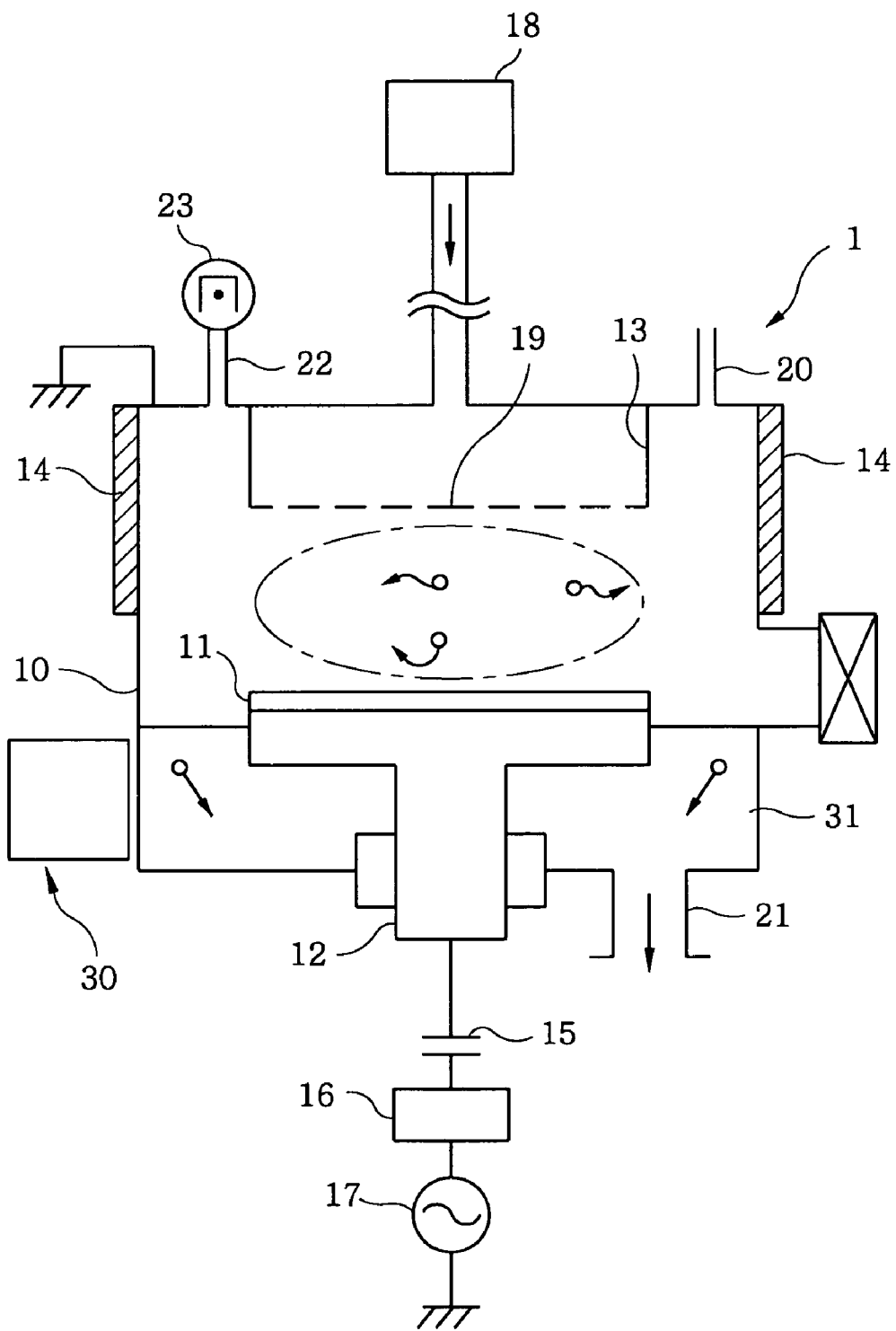
FIG. 1 is a cross sectional view schematically showing the configurations of a processing apparatus in accordance with a preferred embodiment of the present invention.

FIG. 1 is a cross sectional view schematically showing configurations of a processing apparatus in accordance with the preferred embodiment of the present invention.

As shown in FIG. 1, a dry etching apparatus 1 as the processing apparatus for processing an object to be processed includes a vacuum processing chamber 10 whose inside is maintained at a vacuum state for performing an etching process on a wafer 11 as the object to be processed; an exhaust section 31, provided at a lower portion in the vacuum processing chamber 10, for exhausting an inner space of the vacuum processing chamber 10; a lower electrode 12 disposed at a lower portion in the vacuum processing chamber 10, the lower electrode 12 serving also as a mounting table on which the wafer 11 is mounted; an upper electrode 13 disposed to oppositely face the lower electrode 12 from above in the vacuum processing chamber 10; and a heat exchanger 14 installed at an inner wall of the vacuum processing chamber 10. A high frequency power supply 17 is connected to the lower electrode 12 via a blocking capacitor 15 and a high frequency matching circuit 16, and the upper electrode 13 is provided with a plurality of discharge openings 19 through which a gas fed from a gas supply unit 18 for supplying a specified gas is discharged.

Further, there are provided to the vacuum processing chamber 10 an introduction line 20 for introducing a gas into the vacuum processing chamber 10, an exhaust port 21 located at a lower portion in the vacuum processing chamber 10 and connected to an exhausting unit (not shown), and a pressure measuring unit 23 for measuring a pressure in the vacuum processing chamber 10 through a pressure measuring port 22.

In the dry etching apparatus 1, by carrying out an etching cycle wherein an etching process is performed on the wafer 11 on the lower electrode 12, particles 34 are gradually generated in the vacuum processing chamber 10 and float therein. Thereafter, the inside of the vacuum processing chamber 10 is depressurized by the exhausting unit (not shown) and, at the same time, a gas is introduced into the vacuum processing chamber 10 through the introduction line 20, so that particles come to float in the exhaust section 31. In order to monitor the particles 34 floating in the exhaust section 31, a particle monitoring device 30 to be described later is installed at a side portion of the exhaust section 31.

Figure 2:
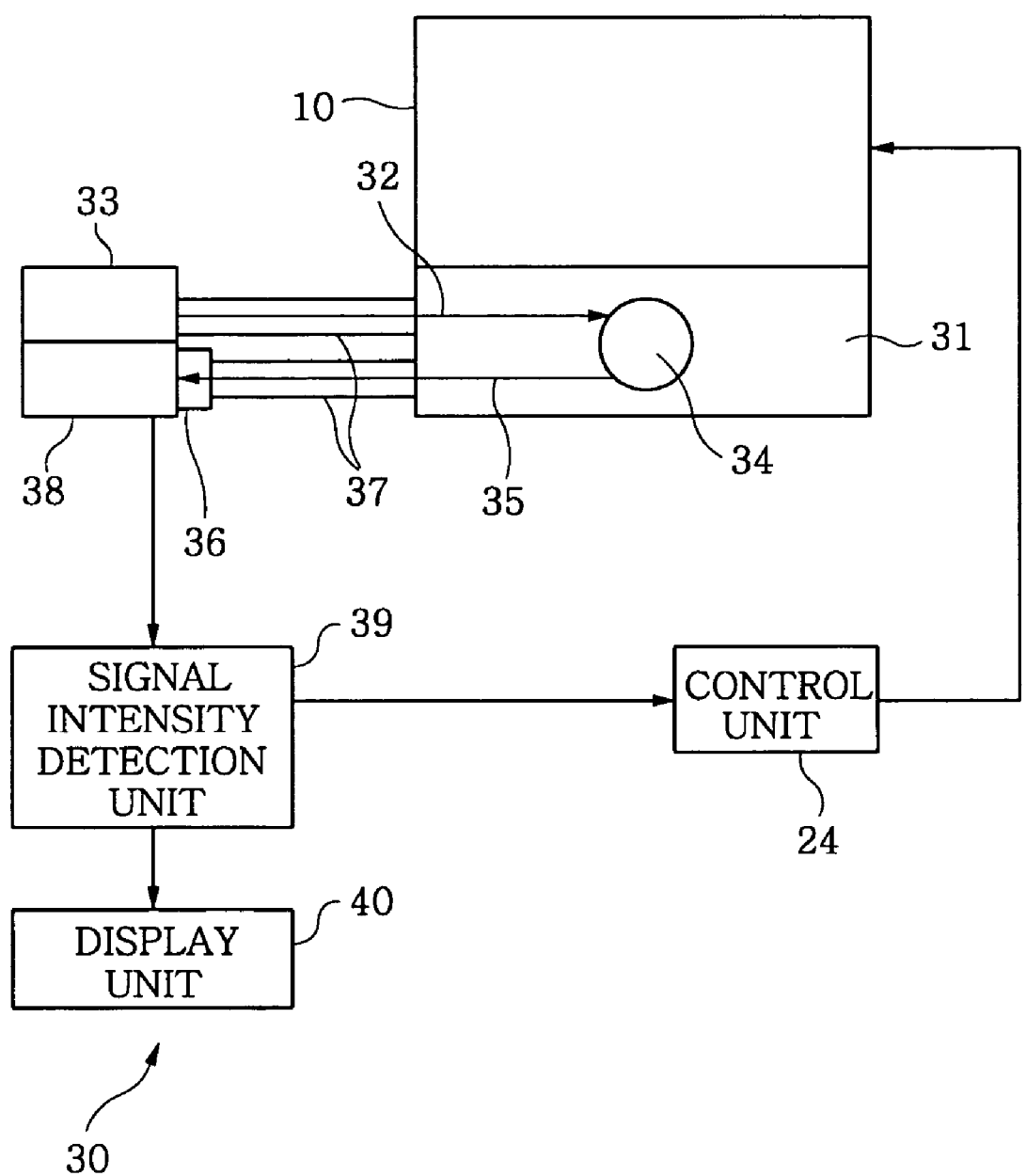
FIG. 2 depicts a schematic view illustrating the configurations of a particle monitoring device in FIG. 1.

FIG. 2 is a schematic view showing configurations of the particle monitoring device in FIG. 1.

In FIG. 2, the particle monitoring device 30 includes a laser beam source (light source) 33 emitting a measurement light 32 such as a YAG laser; an optical fiber (light projecting/receiving unit) 37 for projecting the measurement light 32 into the exhaust section 31 and receiving a scattered light 35 generated by the measurement light 32 being scattered by the particle 34 floating in the exhaust section 31; a received light detection unit 38 for detecting the scattered light 35 received through the optical fiber 37 via an interference filter 36 and converting the scattered light 35 detected into an electrical signal; and a signal intensity detection unit (received light intensity detection unit) 39 which has a received light intensity judgment unit for receiving the electrical signal from the received light detection unit 38 and judging intensity of the electrical signal and also has an instructing unit for outputting an electrical signal to a control device for controlling the etching processing apparatus 1 depending on the judgment result.

The received light detection unit 38 is disposed at a position located along a direction that makes about 180 degrees with respect to the projection direction of the measurement light 32 projected into the exhaust section 31. Further, the optical fiber (light projecting/receiving unit) 37 is disposed such that the scattered light 35 and the measurement light 32 are parallel to (preferably, approximately coaxial with) each other, so that it can project the measurement light 32 and also can receive the scattered light 35. Such optical fiber 37 is isolated from the inside of the chamber by, e.g., a deposition-prevention window (not shown) made of quartz. In addition, the particle monitoring device 30 includes a display unit 40 for receiving the electrical signal from the signal intensity detection unit 39 and displaying a trace of the scattered light depending on the electrical signal.

Furthermore, although the optical fiber 37 receives only the scattered light 35 from the particle 34 in the above description, the present invention is not limited thereto and it may receive scattered lights from plural particles.

In the particle monitoring device 30 constructed as described above, if the measurement light 32 emitted from the laser beam source 33 is projected via the optical fiber 37 into the exhaust section 31 of the vacuum processing chamber 10, the scattered light 35 is generated by the particle 34 floating in the exhaust section 31. The scattered light 35 generated by the particle 34 is received by the optical fiber 37 and is then detected by the received light detection unit 38 via the interference filter 36 to be converted into, e.g., a linear electrical signal corresponding to intensity of the scattered light 35 in a one-to-one relationship.

The electrical signal converted by the received light detection unit 38 is inputted into the signal intensity detection unit 39. The signal intensity detection unit 39 determines whether or not the electrical signal has a value greater than a predetermined value, i.e., whether or not the intensity I of the scattered light 35 is greater than a predetermined intensity $I_0$. The signal intensity detection unit 39 then outputs to the control unit 24 an electrical signal corresponding to the determined result on the intensity I of the scattered light 35. Furthermore, the predetermined intensity $I_0$ is set to be a value selected from plural values determined based on, e.g., an operation status and a process condition of the dry etching apparatus 1 and the like.

By outputting to the control unit 24 the electrical signal corresponding to the determined result on the intensity I of the scattered light 35, the signal intensity detection unit 39 instructs the dry etching apparatus 1 to start, continue or stop the etching process performed on the wafer 11 in the vacuum processing chamber 10 and further instructs a user to perform a cleaning or overhaul of the vacuum processing chamber 10.

Specifically, the signal intensity detection unit 39 instructs the dry etching apparatus 1 to continue the etching process performed in the vacuum processing chamber 10 in case the intensity I of the scattered light 35 is less than the predetermined intensity $I_0$, display on a display device (not shown) thereof an alarm indication for cleaning or overhaul of the vacuum processing chamber 10 in case the intensity I of the scattered light 35 is equal to the predetermined intensity $I_0$, and stop the etching process performed in the vacuum processing chamber 10 in case the intensity I of the scattered light is greater than the predetermined intensity $I_0$.

Further, in a case where an etching cycle is carried out by using a dummy wafer (seasoning) in order to make the atmosphere in the vacuum processing chamber 10 stable under a process condition after cleaning or overhaul has been performed on the inside of the vacuum processing chamber 10, if the signal intensity detection unit 39 determines that the intensity I of the scattered light 35 becomes smaller than a preset intensity $I_t$ ($I_t<I_0$), it is displayed on the display unit (not shown) that the seasoning of the dry etching apparatus 1 has been completed and an etching for the wafer 11 in the vacuum processing chamber 10 is initiated.

Here, typically, the intensity I of the scattered light 35 tends to increase as the diameter of the particle becomes greater. Further, the diameter of the particle affects intensities of a laterally scattered light, a forwardly scattered light and a backwardly scattered light which are respectively scattered in an approximately lateral direction (at about 90 degrees), an approximately forward direction (at about 30~60 degrees) and an approximately backward direction (at about 180 degrees) with respect to the projection direction of the measurement light. Hereinafter, there will be described relationships between intensity of a scattered light generated by a particle, a reception direction of the scattered light with respect to a light projecting direction and a diameter of the particle generating the scattered light.

Figure 3:
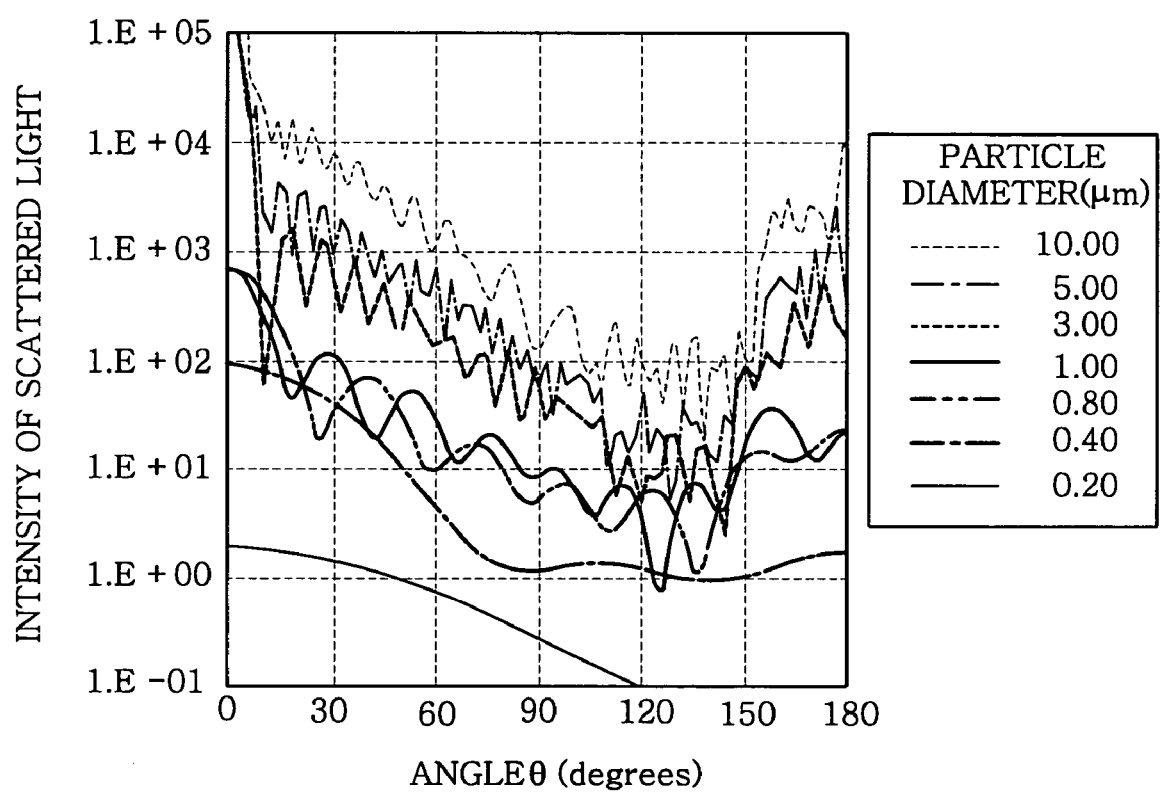
FIG. 3 sets forth a graph showing relationships between intensity of a scattered light, an angle θ representing a reception direction of the scattered light with respect to a projection direction of a measurement light and a diameter of a particle generating the scattered light.
Figure 4:
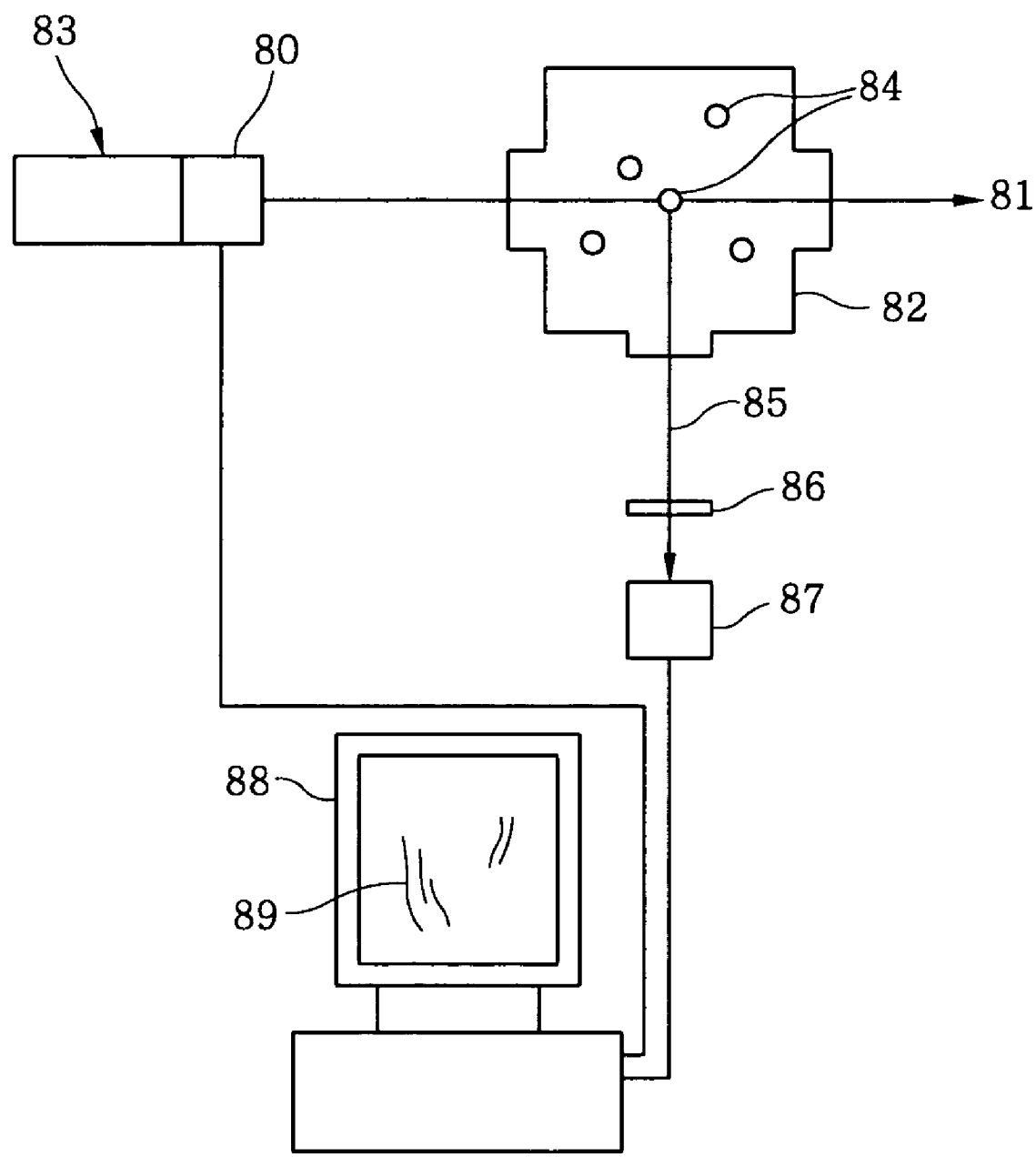
FIG. 4 presents a schematic view showing the configurations of a conventional particle monitoring device.

FIG. 3 is a graph showing relationships between intensity of the scattered light, an angle θ representing the scattered light receiving direction with respect to the light projecting direction and a diameter of the particle.

As shown in FIG. 3, for example, in case the diameter of the particle is 0.4 μm or less, the intensity I of the scattered light increases in the forward direction, i.e., peaking as the angle θ becomes 0 degree. On the other hand, in case the diameter of the particle is 0.8 μm or greater, the intensities of the forwardly and the backwardly scattered light, that are respectively scattered in the approximately forward direction (at about 30~60 degrees) and the approximately backward direction (at about 180 degrees) with respect to the projection direction of the measurement light, become substantially equal to each other.

Here, in the vacuum processing chamber 10 of the dry etching apparatus 1, it is believed that relatively large particles having diameters of about 0.8~1.0 μm are accidentally produced during an etching cycle and affect a contamination of an object being processed. From the results in FIG. 3, by disposing the scattered light receiving unit at an approximately backward position (at about 180 degrees) with respect to the projection direction of the measurement light 32, i.e., by disposing the optical fiber 37 such that the scattered light is received parallel to (preferably approximately coaxial with) the measurement light, a backwardly scattered light having intensity substantially equal to that of a forwardly scattered light can be received, thereby making it possible to monitor the particles which are accidentally produced during the etching cycle and float in the vacuum processing chamber 10.

In accordance with the preferred embodiment described above, since the optical fiber 37 is isolated from the inside of the chamber by the deposition-prevention window (not shown), it is not necessary to install the light projecting unit and the light receiving unit of the optical fiber 37 inside the vacuum processing chamber 10, thereby preventing deterioration in capability of the light projecting unit and the light receiving unit due to the influence of the temperature in the vacuum processing chamber 10. Further, in a case where the optical fiber 37 is installed inside the vacuum processing chamber 10, the optical fiber 37 is disposed in a manner that the scattered light 35 is received substantially parallel to (preferably approximately coaxial with) the measurement light 32, so that a volume occupied by the optical fiber 37 as the light projecting unit and the light receiving unit can be reduced, thereby making it possible to monitor the particles floating in the vacuum processing chamber 10 without deteriorating the exhaust capability of the dry etching apparatus 1.

In accordance with the preferred embodiment, since the signal intensity detection unit 39 determines whether or not a detected intensity I is greater than the predetermined intensity $I_0$ and instructs the dry etching apparatus 1 to start, continue or stop the processing operation on the wafer 11 based on the determined result, any contamination of the wafer 11 due to the particles can be prevented in advance, increasing throughput of the wafer 11.

In accordance with the preferred embodiment, since the optical fiber 37 is connected to the exhaust section 31, it is possible to monitor the particles floating in the exhaust section 31 of the vacuum processing chamber 10 without deteriorating the exhaust capability of the dry etching apparatus 1.

In this preferred embodiment, although the laser beam source 33 emits the measurement light 32 such as a YAG laser, the present invention is not limited thereto. The laser beam source 33 may emit a phase conjugate light of the measurement light 32, that includes a laser such as a YAG laser. In this case, the measurement light 32 is further emitted as the phase conjugate light through a phase conjugate mirror (not shown) for compensating a wave surface distortion. In this way, the laser beam source 33 irradiates through the optical fiber 37 the phase conjugate light of the measurement light 32 toward the particle 34 floating in the vacuum processing chamber 10, so that phase distortion occurring in transmission by using the optical fiber 37 can be eliminated, thereby making it possible to precisely monitor particles floating in the vacuum processing chamber 10.

In this preferred embodiment, while the optical fiber 37 receives the scattered light 35 generated by the measurement light 32 being scattered by the particle floating in the exhaust section 31, the present invention is not limited thereto and the optical fiber 37 may receive an emission light of the particle 34.

In this preferred embodiment, although the received light detection unit 38 converts the scattered light 35 generated by the particle 34 into a linear electrical signal corresponding to the intensity of the scattered light 35 in a one-to-one relationship, it is not limited thereto and may convert the scattered light 35 into a nonlinear electrical signal corresponding to the intensity of the scattered light 35 in a one-to-one relationship.

Further, as the received light detection unit 38 described above, any photoelectric conversion device such as a CCD, a photo multiplier and a channel multiplier may be used. Moreover, a spectrometer may be mounted in front of the received light detection unit 38.

In the preferred embodiment, there has been described the dry etching apparatus 1 as the processing apparatus. However, the processing apparatus is not limited thereto and may be any one selected from a group consisting of a plasma processing apparatus, a heat-treatment apparatus, a film forming apparatus and an ashing apparatus. Further, as the vacuum processing chamber 10 described above, a depressurized vessel such as a processing chamber wherein a specified process, e.g., a plasma processing is performed on the wafer 11 may be employed. The present invention includes any modification of or any addition to the configuration of the processing apparatus made without departing from the spirit of the invention.

In this preferred embodiment, although there has been described the wafer 11 as the object to be processed, the present invention is not limited thereto. The object to be processed may be a semiconductor substrate, a flat panel display (FPD) substrate or a LCD substrate.

While the invention has been shown and described with respect to the preferred embodiments, it will be understood by those skilled in the art that various changes and modification may be made without departing from the spirit and scope of the invention as defined in the following claims.

What is claimed is:

1. A particle monitoring device for monitoring particles in a depressurized space, the particle monitoring device being provided to a processing apparatus, having a depressurized vessel, for processing an object to be processed in the depressurized space demarcated from the depressurized vessel, the particle monitoring device comprising:

a light source for emitting a measurement light; and a light projecting and receiving unit, connected to the depressurized vessel, for projecting the emitted measurement light into the depressurized vessel and receiving a scattered light from a particle floating in the depressurized vessel, wherein the light projecting and receiving unit is disposed such that the scattered light is received substantially parallel to the measurement light.

2. The device of claim 1, further comprising:

a received light intensity detection unit for detecting intensity of the scattered light received by the light projecting and receiving unit, wherein the received light intensity detection unit includes a received light intensity judgment unit for determining whether or not the detected intensity is greater than a predetermined value and an instruction unit for instructing the processing apparatus to start, continue or stop a processing operation of the processing apparatus depending on the determined result.

3. The device of claim 1, wherein the depressurized vessel includes an exhaust section for exhausting the depressurized space thereof, and the light projecting and receiving unit is connected to the exhaust section.

4. The device of claim 1, wherein the light projecting and receiving unit is an optical fiber.

5. The device of claim 4, wherein the measurement light is further emitted as a phase conjugate light.

6. The device of claim 1, wherein the depressurized vessel is a processing chamber for a plasma processing.

7. Amended) The device of claim 1, wherein the light projecting and receiving unit is disposed such that the scattered light is received approximately coaxial with the measurement light.

8. A processing apparatus comprising the particle monitoring device recited in claim 1.

* * * * *